United States Patent
Naik et al.

(10) Patent No.: US 10,553,304 B2
(45) Date of Patent: Feb. 4, 2020

(54) METHOD AND APPARATUS FOR REDUCING CHEMICAL REACTION MECHANISMS

(75) Inventors: Chitralkumar V. Naik, San Diego, CA (US); Cheng Wang, San Diego, CA (US)

(73) Assignee: Ansys, Inc., Canonsburg, PA (US)

( * ) Notice: Subject to any disclaimer, the term of this patent is extended or adjusted under 35 U.S.C. 154(b) by 154 days.

(21) Appl. No.: 13/446,839

(22) Filed: Apr. 13, 2012

(65) Prior Publication Data

US 2012/0290280 A1 Nov. 15, 2012

Related U.S. Application Data (60) Provisional application No. 61/475,122, filed on Apr. 13, 2011.

(51) Int. Cl.
*G01N 31/00* (2006.01)
*G16C 20/10* (2019.01)

(52) U.S. Cl.
CPC ................................. *G16C 20/10* (2019.02)

(58) Field of Classification Search
None
See application file for complete search history.

(56) References Cited

U.S. PATENT DOCUMENTS

| | | |
|---|---|---|
| 6,212,488 B1 | 4/2001 | Meier et al. |
| 2003/0004696 A1 | 1/2003 | Yamazaki |
| 2011/0010150 A1 | 1/2011 | Palsson |

OTHER PUBLICATIONS

Mallison et al. "Detailed Chemical Kinetics Study of the Role of Pressure in Butane Pyrolysis" (Ind. Eng. Chem. Res. vol. 31 (1992) pp. 37-45).*

Pepiot Desjardins et al. An automatic chemical lumping method for the reduction of large chemical kinetic mechanisms. Combustion Theory and Modelling 12:1089-1108. Nov. 15, 2008. Retrived from the internet: <URL:http://web.mae.cornell.edu/pepiot/pdf/Pepiot_CTM_2008.pdf>.

Alberty et al. Stanford chemical thermodynamic properties of alkene isomer groups. Journal of Physical Chemistry 14:803-820. 1985. Retrieved from the internet: <URL:http://www.nist.gov/data/PDFfiles/jpcrd279.pdf>.

Notification of Transmittal of the International Search Report and the Written Opinion for PCT/US2012/033599, dated Jul. 13, 2012.
Written Opinion of the International Searching Authority for PCT Application PCT/US2012/0335599, dated Jul. 13, 2012.
Ahmed, S.S., "Reduced Mechanism for the Oxidation of the Mixtures of n-Heptane and iso-Octane", Division of Combustion Physics, Lund University, Lund, Sweden, Proceedings of the European Combustion Meeting 2005, 5 pages.
Ahmed, Syed Sayeed, "A Comprehensive and Compact n-heptane Oxidation Model Derived Using Chemical Lumping", Phys. Chem. Chem. Phys., 2007, pp. 1107-1126.
Lu, Tianfeng et al., "Directed Relation Graph with Expert Knowledge for Skeletal Mechanism Reduction", 2011 7th US National Combustion Meeting, Atlanta, Georgia, Mar. 20-23, 2011, 10 pages.
Lu, Tianfeng et al., "Strategies for Mechanism Reduction for Large Hydrocarbons: n-Heptane", ScienceDirect, Combustion and Flame 154, 2008, pp. 153-163.
Ranzi, E. et al., "Lumping Procedures in Detailed Kinetic Modeling of Gasification, Pyrolysis, Partial Oxidation and Combustion of Hydrocarbon Mixtures", Progress in Energy and Combustion Science, 2001, pp. 99-139.
Extended European Search Report dated Feb. 26, 2015 from related/corresponding European Patent Application 12771638.9-1951, filed Apr. 13, 2012.
Communication Pursuant to Article 94(3) EPC from the European Patent Office dated Nov. 24, 2016 from related / corresponding EP Application No. 12771638.9.
Office Action dated Jul. 20, 2018 from related Korean Application No. 10-2013-7029910 with English translation.

\* cited by examiner

*Primary Examiner* — Anna Skibinsky
(74) *Attorney, Agent, or Firm* — Jones Day (57) ABSTRACT

Method and apparatus for reducing chemical reaction mechanisms are disclosed. A method comprises obtaining data for one or more chemical species in a chemical reaction model from a database, the database including properties of the one or more chemical species; grouping the chemical species in a chemical reaction model into one or more isomer groups according to molecular properties of the chemical species; assigning a representative isomer to at least one isomer group; replacing, in one or more chemical reaction equations of the chemical reaction model, one or more groups of chemical species with a corresponding representative isomer; and executing the chemical reaction model by an apparatus to determine results.

19 Claims, 3 Drawing Sheets

METHOD AND APPARATUS FOR REDUCING CHEMICAL REACTION MECHANISMS

RELATED APPLICATIONS

This application claims the benefit under 35 U.S.C. § 119(e) to U.S. Provisional Patent Application Ser. No. 61/475,122, filed Apr. 13, 2011, which is incorporated by reference in its entirety and for all purposes.

TECHNICAL FIELD

The present application relates generally to chemical reaction simulation models and, more particularly, to generating reduced reaction mechanisms.

BACKGROUND

Complex chemical reaction mechanisms involve large numbers of interrelated individual reactions and chemical species. The analysis of complex chemical reactions under various conditions (i.e., modeling) requires solving numerous mathematical equations that represent the individual species, taking into account reaction conditions of interest, reaction rate constants and the properties and quantities of various individual species. Reaction kinetics of the combustion process, in particular, can involve thousands of discrete reactions and chemical species. Analyzing complex chemical processes by solving the numerous representative mathematical equations associated with detailed reaction models (mechanisms) consumes vast computing resources and requires long run-times, especially over varied reaction conditions. Even relatively small increases in the number of chemical species involved may greatly increase computational storage requirements and processing, due in part to the increased number of calculations required to account for interdependencies between the species equations.

Reaction mechanisms are a fundamental tool for accurately analyzing complex chemical reaction processes, such as combustion, for example. A mechanism includes data representing the reactions and species in a chemical process, compiled in a way to allow mathematical simulation of the process to determine the chemical composition (state) of the system at a given time or location in space. Such chemical composition (amount of each species or molecule in the system) may be expressed as representative mathematical equations, or components thereof, that are operable and solvable. Detailed multi-purpose mechanisms have been developed through various means and methods to represent and simulate various types of chemical species and reactions, including by solving associated representative equations. However, very detailed reaction mechanisms are often of limited value in analyzing complex chemical processes, because running simulations that include all the species in such mechanisms, which are large enough to accurately capture the range of conditions in a modern combustion system, for example, is prohibitive in terms of computing time required. Generation of accurate reduced reaction mechanisms to represent complex chemical reactions requires significant effort and time. Increasing the efficiency and accuracy of the mechanism-reduction process facilitates more rapid and efficient research and development in the field of chemical reactions, especially for combustion systems.

SUMMARY

Various aspects of examples of the invention are set out in the claims.

According to a first aspect of the present invention, a method comprises accessing data representing a master mechanism associated with a chemical reaction model, identifying one or more chemical reaction equations and associated chemical species in the master mechanism, grouping the chemical species into one or more isomer groups according to molecular properties of the chemical species, assigning a representative isomer to each isomer group, and replacing each chemical species that belongs to an isomer group and its properties with a representative isomer structure and associated representative properties that correspond to the respective isomer group of the master mechanism. A reduced mechanism may thus be generated based on the master mechanism, for use in analyzing the chemical process. It is to be appreciated that chemical species and reactions in a master mechanism may be expressed as representative mathematical equations or components thereof, that are operable and solvable.

A second aspect of the present invention provides a method for generating a reduced chemical reaction mechanism for a chemical reaction model. This method may be characterized by the following operations: (a) accessing data representing a master mechanism associated with a chemical reaction model, the master mechanism including a set of chemical reaction equations, a set of associated chemical reaction variables, and a set of associated chemical species; (b) selecting target output variables from the set of chemical reaction variables; (c) assigning error tolerances to the target output variables; (d) solving the chemical reaction equations for the selected target output variables and designating these solution values as master values; (e) performing an iterative isomer lumping process characterized by: (i) categorizing the chemical species in the master mechanism into isomer groups according to molecular structure and properties, by applying one or more isomer lumping rules; (ii) replacing each chemical species categorized as belonging to an isomer group, and its associated properties, with a representative isomer and representative set of properties to generate a provisional mechanism; (iii) solving the chemical reaction equations for the target output variables, using the provisional mechanism; (iv) calculating an error value for each target output variable, by comparing each master value with the value of the corresponding target output variables found using the provisional mechanism; (v) applying a successive isomer lumping rule to replace more species with representative isomers until the maximum error value for any target output variable is greater than a predetermined threshold value; and (f) identifying the provisional mechanism with the least number of species resulting in all error values less than the predetermined threshold value as the reduced mechanism.

In an aspect of the invention, the master mechanism may include chemical reaction paths. Another embodiment may include an additional operation of defining a set of chemical reaction-flow models that represents certain operating conditions and in which the chemical reaction equations may be conservation equations that include variables and mathematical terms derived from the chemical reaction model. Such chemical reaction equations and conservation equations may be expressed as mathematical equations that are operable and solvable. Target output variables may be selected from the set of reaction-flow model conservation equations as described above, and the conservation equations may be solved to generate master values for these variables. The chemical species in these reaction-flow model conservation equations may be categorized into isomer groups and replaced with representative isomers and properties and the conservation equations may be iteratively solved, with successive species replacement by isomers, as discussed above, to iteratively generate target output variables until the maximum error value for any target output variable is greater than a predetermined threshold, as discussed above.

It is to be appreciated that the predetermined threshold value may be set as a numerical value, and that this predetermined threshold value may be set as 1 in embodiments of the invention. In other embodiments, at least one of the isomer lumping rules and the sequence of applying the rules may be predetermined. In still other embodiments, during the course of generating the reduced mechanism, one or more of the isomer lumping rules may be accessed from a database or other compilation of isomer lumping rules, or the sequence of applying isomer lumping rules may vary depending on the outcome of each iteration.

Another aspect of the invention pertains to apparatus and computer program products, including machine-readable media on which program instructions and/or arrangements of data for implementing the methods described above may be provided. For the performance of certain method operations, program instructions may be provided as computer code. Data, if employed to implement features of embodiments of this invention, may be provided as data structures, database tables, data objects, or other appropriate arrangements of specified information. Any of the methods of this invention may be represented, in whole or in part, as program instructions and/or data provided on machine-readable media.

BRIEF DESCRIPTION OF THE DRAWINGS

For a more complete understanding of example embodiments of the present invention, reference is now made to the following descriptions taken in connection with the accompanying drawings in which.

DETAILED DESCRIPTION OF THE DRAWINGS

Figure 1:
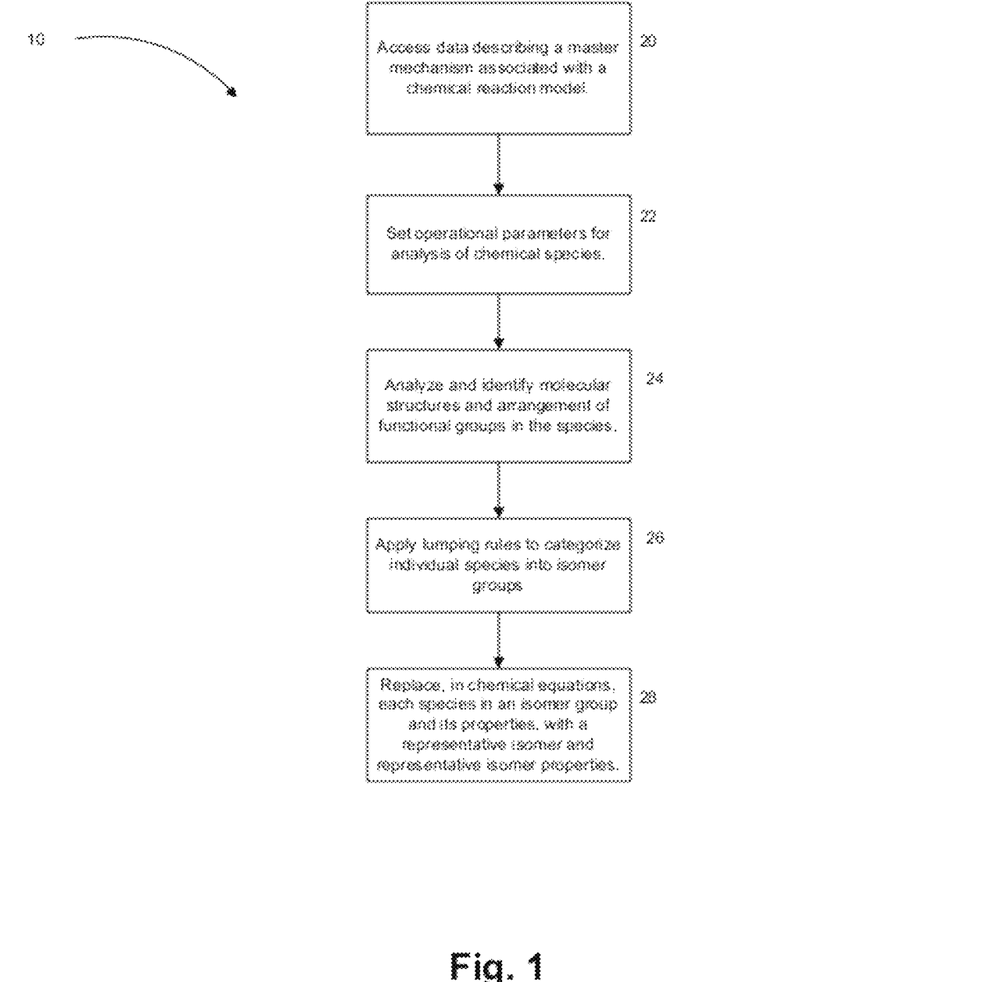
FIG. 1 is a flow chart illustrating a method according to one embodiment.
Figure 2:
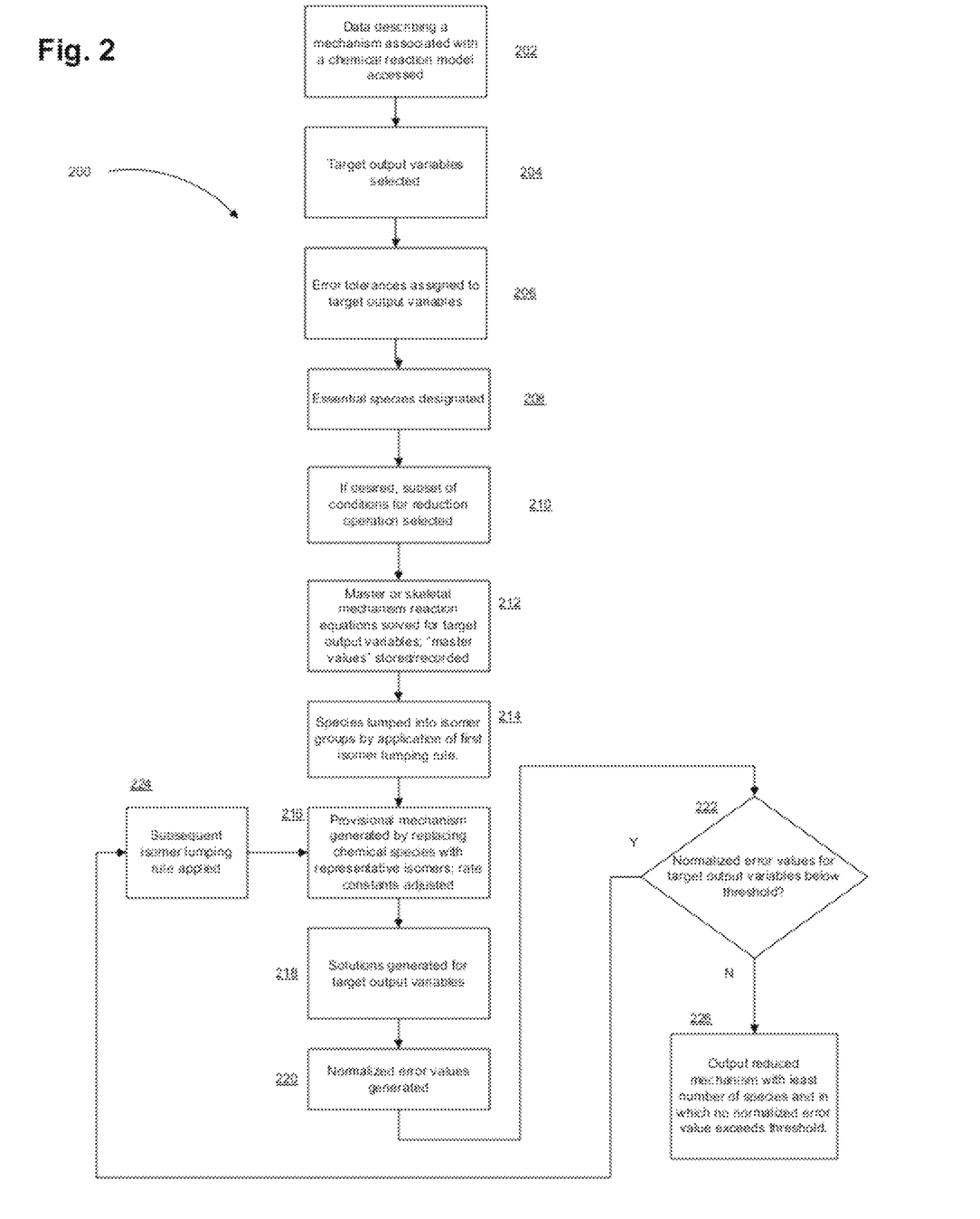
FIG. 2 is a flow chart illustrating a method according to another embodiment.
Figure 3:
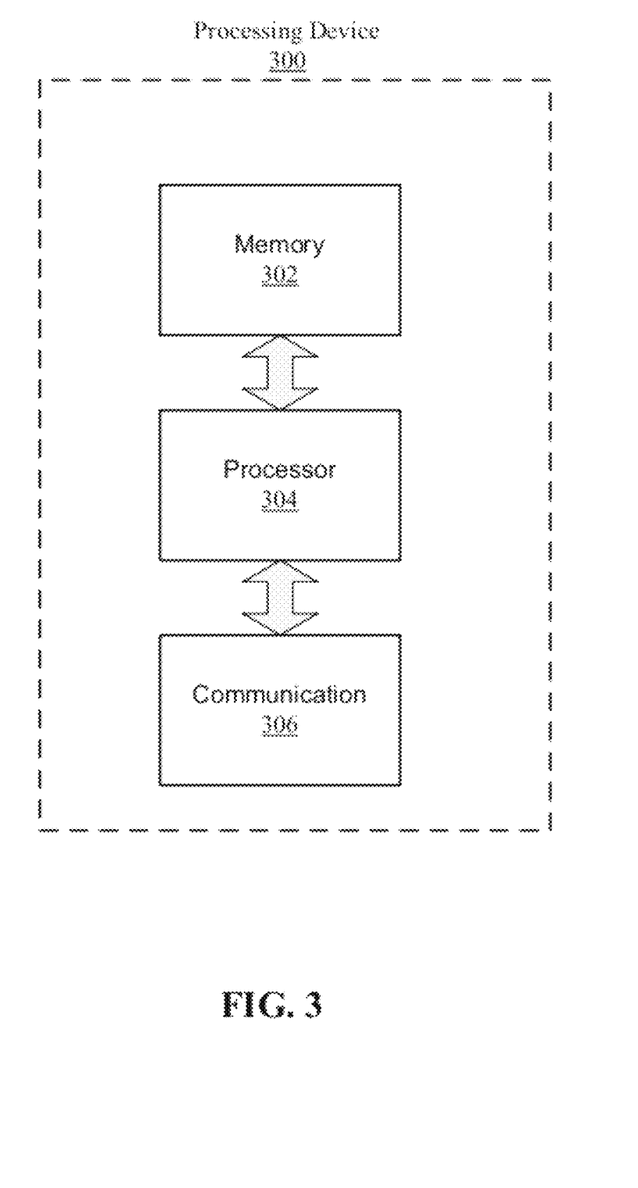
FIG. 3 illustrates an exemplary device within which the various embodiments may be implemented.

Example embodiments of the present invention and their potential advantages are understood by referring to FIGS. 1-3 of the drawings.

Even with an appropriate mechanism, however, analyzing the myriad equations in a complex chemical reaction model requires a large amount of time and computational resources, due to the sheer numbers and interrelations of the reactions, species and conditions involved for each simulation of the chemical reaction. Running repeated simulations over varied reaction conditions requires even more time.

Several methods of chemical reaction mechanism reduction have evolved, to generate more manageable mechanisms for analysis, such as sensitivity analysis, principal component analysis, detailed reduction, lumping, and adaptive reduction approaches for generating reduced mechanisms. In particular, species lumping is a mechanism reduction process that generates reduced mechanisms with fewer distinct species than the pre-reduction mechanism. Accurate reduced mechanisms may be generated by a process of identifying and grouping together species that have similar molecular structures and properties, and replacing, in the mechanism, each species that belongs to a particular group, with an isomer having a set of properties that is representative of the species in the respective group.

In accordance with the present invention, methods are presented for generating reduced mechanisms from master mechanisms representing large chemical reaction models. The reduced mechanisms generated by these methods include fewer distinct reaction species than the corresponding master mechanisms and thus require fewer calculations and less time to run a simulation of the chemical reaction model. In fact, the time-savings achieved by employing accurate reduced mechanisms to analyze chemical reaction models becomes increasingly pronounced when the analysis is performed over a wide range of conditions.

Although reducing the number of species in chemical reaction mechanisms reduces their complexity and the time required to solve the respective equations, this method of mechanism reduction also decreases the accuracy of the reduced mechanism. A lumping approach characterizes species in a mechanism based on molecular structures and properties. A reduced mechanism is generated by analyzing chemical species in a chemical reaction mechanism based on molecular structure and properties, lumping the species into isomer groups based on these characteristics, in light of a set of one or more isomer lumping rules, which may be predetermined in whole or in part, and substituting representative isomers and properties for corresponding species in the mechanism reaction equations. Since similar species are replaced by a single representative isomer, the overall number of distinct species in the mechanism is reduced. In an embodiment, accuracy of the mechanism reduction process is controlled by an iterative process of applying an isomer lumping rule, from a set of rules, to generate a provisional mechanism with a reduced number of species and modified chemical reaction equations, solving the chemical reaction equations in the provisional mechanism, evaluating the solutions to determine a respective error value, and, if the error values are within acceptable limits, applying a successive isomer lumping rule, from the set of rules, to generate another provisional mechanism with still fewer species. This iterative process is repeated until an error value falls outside acceptable limits. The provisional mechanism having the least number of species for which the acceptable error limits are satisfied is the reduced mechanism.

I. Standalone Mechanism Reduction Employing Isomer "Lumping."

A feature of the methods described in connection with the invention is a procedure for reducing chemical reaction mechanisms by grouping chemical reaction species into isomer groups based on the molecular properties of the species, and replacing, in the chemical reactions, each species belonging to a particular isomer group and its properties, with a representative isomer and a representative set of properties. Replacing a number of distinct chemical reaction species with a reduced number of substituted isomers simplifies the number and complexity of calculations required to run a chemical reaction model simulation.

Referring now to FIG. 1, a flow chart illustrates a method according to one embodiment. Various operations shown in FIG. 1 may be performed in the order depicted or in some other order. In accordance with the method of FIG. 1, a mechanism reduction process 10 begins at block 20, as data describing a master mechanism associated with a chemical reaction model is accessed. The data may be accessed from a database of various chemical species and their associated properties, for example. The data includes chemical reaction equations and chemical species representing chemical processes in the chemical reaction model, along with data representing equation variables and constant values (e.g., thermodynamic rate constants), as well as the molecular structure, functional groups, and thermodynamic property data regarding the chemical species in the master mechanism. The master mechanism may be a novel mechanism, or may be a mechanism that has been used in previous chemical reaction modeling studies, and may be accessed from a library, or generated as part of a broader chemical reaction model analysis that incorporates this process 10 to reduce the master mechanism. In any case, the master mechanism and related data may be generated in accordance with principles and by various techniques. In addition, it is to be appreciated that chemical species and reactions in a master mechanism may be expressed as representative mathematical equations, or components thereof, that are operable and solvable.

After the data describing the master mechanism is accessed (block 20), the operational parameters of the process 10 are set, as shown at block 22. These parameters control subsequent steps of the process 10, particularly the analysis and categorization of species into isomer groups (blocks 24 and 26). As will be described in greater detail below, in one embodiment, setting operational parameters may include specifying the maximum difference in the values of chemical species thermodynamic properties such as enthalpy and/or entropy that is acceptable among all chemical species categorized into an isomer group. Only species with properties meeting this operational parameter will be included in a corresponding isomer group. Of course, in keeping with the invention, other thermodynamic properties can be used in a similar fashion for categorizing species into isomer groups. As noted above, a database of chemical species and their associated properties, such as thermodynamic properties, may be used in this regard.

In an embodiment of the invention, the master mechanism may include chemical reaction paths. In yet another embodiment, specifying the reaction conditions as discussed above (block 22) may also include defining a set of chemical reaction-flow models that represents certain operating conditions and in which the chemical reaction equations of the master mechanism may be conservation equations that include variables and mathematical terms derived from the chemical reaction model. Such chemical reaction equations and conservation equations may be expressed as mathematical equations that are operable and solvable. The chemical species in these reaction-flow model conservation equations may be categorized into isomer groups and replaced with representative isomers and properties in the process of generating a reduced mechanism.

Once operational parameters are specified for process 10 (block 22), each chemical species' molecular structures and arrangements of functional groups may be analyzed, as indicated at block 24. In an embodiment, this analysis may identify the number of carbon atoms in all of the straight chain of branched chain species, as well as the number and positions of carbon-carbon atomic bonds and particular functional groups in each of the species, such as hydroxy, hydroxyl radical, carbonyl, peroxide, peroxy radical, and carbon radical groups. Similarities in the molecular structures and positioning of chemical species' functional groups tend to reflect similarities in the chemical species' properties for purposes of chemical reaction analysis, particularly regarding hydrocarbon species such as those in combustion reactions.

Thus, similarities between the structures of chemical species allow for the substitution of representative isomers and representative properties for similar species in chemical reaction equations, because the behavior and properties of a single carefully selected representative isomer in a reaction can approximate the behavior and properties of several similar chemical species. Generating reduced mechanisms by decreasing the number of distinct chemical species, their respective properties, and associated interrelations with other species in chemical reaction models simplifies the mechanism in question, thus facilitating faster simulations and analysis.

After the molecular structure and properties of each chemical species has been analyzed and identified, the process categorizes, or groups, individual species into isomer groups based on similarities in the species' molecular structures and properties (block 26). This categorization process may be referred to as "lumping." In an embodiment, the lumping process may proceed in accordance with a predetermined series of lumping rules. It is to be appreciated that, in keeping with the invention, other combinations of lumping rules may be applied, or lumping rules may be applied in a different sequence than set forth below, or that not all of the lumping rules set forth below must be applied. In other embodiments, the series of lumping rules may be selected from a list or library containing such predetermined lumping rule series.

As discussed earlier the following functional groups may be considered in the lumping process: hydroxy, hydroxyl radical, carbonyl, peroxide, peroxy radical, and carbon radical groups. In an embodiment, species are considered to be candidates for isomers if they satisfy the following isomer lumping rules:

They have the same number of each of the functional groups

Their main carbon chains (i.e. without considering the attachments of all functional groups), including all carbon branches, are identical If the species are unsaturated species (i.e. alkenes), the locations of carbon-carbon double or triple bond on the main chains are identical For analysis of low-temperature kinetic reactions, two additional rules are implemented 1. The relative position of the carbon radical site to the peroxy group is identical between the species for the following conditions:

the carbon radical site is adjacent to the carbon site where peroxy group is attached the carbon radical site is exactly at 2nd position from the carbon site where peroxy group is attached the carbon radical site is exactly at 3rd position from the carbon site where peroxy group is attached 2. The relative position of the carbon sites where the peroxy radical group is attached is identical between the species for the following conditions:

the two carbon sites are adjacent to each other there is exactly one carbon atom between the two carbon sites there are exactly two carbon atoms between the two carbon sites The results on which these two additional rules are based, along with additional details, can be found in S. S. Ahmed, F. Mauss, G. Moreac, and T. Zeuch, "A Comprehensive and Compact n-Heptane Oxidation Model Derived Using Chemical Lumping," *Phys. Chem. Chem. Phys.*, 9: 1107-1126, 2007.

Analyzing chemical species and categorizing, or lumping, the species into isomer groups by application of isomer lumping rules results in one or more groups of chemical species with similar structures and properties. The groupings may be recorded or stored for further analysis.

At this point an additional lumping rule based on the values of standard enthalpy of formation of species may be applied: an isomer group of species will be divided into sub-groups if the maximum difference in standard enthalpy of formation among the species is beyond a certain threshold value. As discussed above, this threshold value may be set as an operational parameter as shown at block 22 of FIG. 1. As a result of applying this lumping rule, any group of species will exhibit a difference in standard enthalpy of formation within a pre-defined level. The discrepancy in this property between the lumped species and representative isomers will thus be minimized, and the accuracy of the reduced mechanism will be improved. In an embodiment, a threshold value for maximum allowed difference in standard enthalpy of formation among lumped species is 5 kcal/mole in order to generate the smallest lumped mechanism while maintaining the highest level of accuracy.

Once chemical species are categorized into isomer groups based on lumping rules, each species in the isomer group is replaced, in the chemical reaction equations of the master mechanism, by a single representative isomer, as shown at block 28 of FIG. 1. This means that all thermodynamic and transport properties of each species belonging to an isomer group are replaced by properties of the respective representative isomer. Accordingly, all chemical reaction equations in the master mechanism that involve a species in a particular isomer group are thus modified to include the respective representative isomer and the representative properties. Data and properties corresponding to representative isomers may be accessed from a compilation or library or database of representative isomers for inclusion in the equations of a mechanism undergoing reduction. That said, other specific isomer data and properties that rely on the number and types of species in the isomer group may be calculated as part of the mechanism reduction process, as described in greater detail, below.

Because each representative isomer replaces several distinct chemical species, the thermodynamic and transport properties of a representative isomer are combinations of the corresponding properties of each chemical species in the isomer group. Various methods of accounting for the contributions of each chemical species are known in the art, and detailed descriptions of them are not central to the invention, and are beyond the scope of this disclosure. In an embodiment of the invention, an equi-repartition approach is applied. This approach is known by persons of skill in the art, and described in S. S. Ahmed, G. Moreac, T. Zeuch, and F. Mauss, "Reduced Mechanism for the Oxidation of the Mixtures of n-Heptane and iso-Octane," European Combustion Meeting, 2005. This equi-repartition approach assumes that each chemical species in an isomer group makes the same contribution to the representative isomer properties, so that the relative contribution of such a chemical species is the reciprocal number of chemical species in the isomer group. The process 10 can implement this process very simply, and the only input required is the mechanism itself. Although the equi-repartition method may lead to reduced accuracy, as compared with another method described in detail, below, the equi-repartition approach complements the standalone mechanism reduction process 10, because a reduced mechanism can be generated utilizing an isomer lumping procedure that does not require any inputs beyond the mechanism itself.

I.A. Adjustment of Rate Constants

Equations representing chemical reactions incorporate rate constants that quantify reaction speed. Since rate constants depend on the properties of the species in the equation, replacement of chemical species with isomers as part of a mechanism-reduction procedure also requires adjustment of rate constants in the reactions or equations, to account for the properties of the "replacement" representative isomer. The forward and reverse rate constants are related by the equilibrium constants in the respective reaction equations. Although the specific details of the kinetic theory are beyond the scope of this disclosure, and are not required to understand the invention, in an embodiment of the invention, in an embodiment, three types of adjustments may be made for the rate constants in the chemical reactions of the mechanism:

1. If the reaction represented by the particular reactions or equation(s) in question is reversible, and the equilibrium constant is used to calculate the reverse rate constant from the forward rate constant, both the forward rate constant and the equilibrium constant require adjustment.
2. If the reaction represented by the particular equation(s) in question is reversible and the reverse rate constant is defined explicitly, both the forward rate constant and the reverse rate constant require adjustment.
3. If the reaction represented by the particular equation(s) in question is irreversible, only the forward rate constant requires adjustment.

For example, consider $\{A_i\}$ and $\{B_i\}$ as representing two isomer groups, and $A_i$ and $B_i$ represent a species from each group. $L_A$ is the reciprocal of the relative contribution of $A_i$ to the group $\{A_i\}$ and $L_B$ is the reciprocal of the relative contribution of $B_i$ to the group $\{B_i\}$. If the equi-repartition approach is utilized, $L_A$ equals the number of isomers in the $\{A_i\}$ group and $L_B$ equals the number of isomers in the $\{B_i\}$ group.

Species C and D do not belong to any group of isomers. If the reaction is reversible and the equilibrium constant is used to calculate the reverse rate constant from the forward rate constant, the reverse rate constant is calculated using the following formula:

$$k_r = k_f / k_{eq}$$

The following adjustments will be applied to the forward rate constant and the equilibrium constant:

| | | |
|---|---|---|
| $A_i + C = D$; | $k_{fnew} = k_{fold}/L_A$, | $k_{eqnew} = k_{eqold}/L_A$ |
| $A_i + B_i = C + D$; | $k_{fnew} = k_{fold}/(L_A * L_B)$, | $k_{eqnew} = k_{eqold}/(L_A * L_B)$ |
| $D = A_i + C$; | $k_{fnew} = k_{fold}$, | $k_{eqnew} = k_{eqold} * L_A$ |
| $C + D = A_i + B_i$; | $k_{fnew} = k_{fold}$, | $k_{eqnew} = k_{eqold} * (L_A * L_B)$ |
| $A_i + C = B_i + D$ | $k_{fnew} = k_{fold}/L_A$, | $k_{eqnew} = k_{eqold} * (L_B/L_A)$ |

If a reversible reaction in the mechanism is using an explicit reverse rate constant, the following adjustment will be applied to the forward rate constant and the reverse rate constant:

| | | |
|---|---|---|
| $A_i + C = D$; | $k_{fnew} = k_{fold}/L_A$, | $k_{rnew} = k_{rold}$ |
| $A_i + B_i = C + D$; | $k_{fnew} = k_{fold}/(L_A * L_B)$, | $k_{rnew} = k_{rold}$ |
| $D = A_i + C$; | $k_{fnew} = k_{fold}$, | $k_{rnew} = k_{rold}/L_A$ |
| $C + D = A_i + B_i$; | $k_{fnew} = k_{fold}$, | $k_{rnew} = k_{rold}/(L_A * L_B)$ |
| $A_i + C = B_i + D$; | $k_{fnew} = k_{fold}/L_A$, | $k_{rnew} = k_{rold}/L_B$ |

For irreversible reactions, the following adjustment will be applied to the forward rate constant:

| | |
|---|---|
| $A_i + C => D$ | $k_{fnew} = k_{fold}/L_A$ |
| $A_i + B_j => C + D$ | $k_{fnew} = k_{fold}/(L_A*L_B)$ |
| $D => A_i + C$ | $k_{fnew} = k_{fold}$ |
| $C + D => A_i + B_j$ | $k_{fnew} = k_{fold}$ |
| $A_i + C => B_j + D$ | $k_{fnew} = k_{fold}/L_A$ |

Once these calculations are performed and the values of the adjusted constants are substituted for their corresponding rate constants in the equations, the equations may be solved.

After the isomer lumping rules are applied, representative isomers and representative properties are substituted, in the chemical reaction equations of the master mechanism, for the chemical species in isomer groups. In addition, the equation constants are adjusted, and a reduced mechanism with fewer chemical species results and is in condition for use in the analysis of chemical reaction models. The reduced mechanism may be utilized immediately in analysis of the chemical reactions in the reduced mechanism itself, or incorporated into a larger process of analyzing a chemical reaction model by running simulations that incorporate the reduced mechanism. Alternately, the reduced mechanism may be recorded or stored for these and other uses in the future, whether by itself, or as part of a library of mechanisms. Particular mechanisms in such a library may be retrieved or accessed to facilitate chemical reaction analysis in conditions for which a particular mechanism in the library is appropriate.

Embodiments and methods of the invention may also be incorporated into a larger process of analyzing and simulating chemical reaction models. For example, a method for analyzing chemical reaction models may incorporate mechanism reduction methods of the present invention as a subroutine that is run one or more times during the overall process. Even though a reduced mechanism generated by the "standalone" mechanism reduction method described above may not have been optimized for accuracy, the benefits of applying this method are twofold: the reduced mechanism may be generated very rapidly; and the only input required is the master mechanism. In contrast, more accurate reduced mechanisms may be generated by following other methods described in this disclosure; although generation and analysis of these more accurate reduced mechanisms require more processing time, the generation of target output values using the master mechanism, and the input of additional information beyond the mechanism itself.

II. Mechanism Reduction Employing Iterative Isomer Lumping and Error Tolerances.

Referring now to FIG. 2, a flowchart illustrates a method according to another embodiment. Various operations shown in FIG. 2 may be performed in the order depicted or in some other order. Mechanism reduction process 200 begins by accessing data that describes a master mechanism associated with a chemical reaction model (block 202). As discussed above in connection with another embodiment, above, the data may be available from a database and may include a set of one or more chemical reactions, a set of one or more chemical reaction variables and constant values (e.g., thermodynamic rate constants), along with data representing the molecular structure, functional groups and thermodynamic properties of the chemical species in the master mechanism. In addition, the data may include, among the chemical reaction variables, a set of target output variables such as intrinsic solution variables from a reaction model or equation, as well as derived variables (examples of such derived variables in combustion analysis include flame-speed, ignition-delay data, hear-release data and emission indices).

Also as discussed above, the master mechanism and related data may be wholly or partially novel or previously developed, and may be wholly or partially accessed from a library, or generated as part of a broader chemical reaction model analysis that incorporates the mechanism reduction process 200.

In an alternative embodiment, a skeletal mechanism may be generated from the master mechanism prior to starting the mechanism reduction process, and the data corresponding to the skeletal mechanism may be accessed as shown at block 202. Methods such as the Directed Relation Graph method, for example, are useful in generating skeletal mechanisms. Such methods are not central to this invention, and will not be discussed in detail. Skeletal mechanisms may include the same types of data as those found in master mechanisms (i.e., chemical reaction equations and chemical species representing the chemical reactions in the chemical reaction model, along with data representing equation variables and constant values, such as thermodynamic rate constants, as well as the molecular structure, functional groups, thermodynamic property data regarding the chemical species in the skeletal mechanism, and target output variables). Thus, data accessed as shown at block 202 may correspond to a master mechanism as described in the preceding paragraph, or a skeletal mechanism derived from a master mechanism by employing various methods. In fact, several computational packages exist for the generation of mechanisms and skeletal mechanisms associated with chemical reactions.

After the data describing the master or skeletal mechanism is accessed at block 202, target output variables are selected as shown at block 204. The selected target output variables correspond to the mechanism parameters of interest in the chemical reaction analysis. In an embodiment, the target output variables may be selected from a predetermined list or a library. Such a library may have been previously generated in connection with developing the master or skeletal model for a chemical reaction model analysis.

In an embodiment, the target output variables may also be used in monitoring and controlling the degree of accuracy of the mechanism reduction process 200. As will be discussed in greater detail below, the mechanism reduction process 200 involves the removal of species from mechanisms. The removal of species, in turn, reduces the accuracy of the mechanism, and results in a corresponding increase in a calculated error value (error value calculation described in greater detail below). The assignment of error tolerances to target output variables (block 206) facilitates control of the species removal procedure because, in an embodiment, no more species will be removed from a mechanism than permits compliance with the error tolerances. This control process and the species removal procedure according to the invention are described in greater detail, below.

In an embodiment, relative error tolerances and absolute error tolerances may be assigned to target output variables. For example, assigning an absolute error tolerance value of 1.E-6 mole fraction may be appropriate for species fractions such as PPM of NOx. In this example, species removal would proceed for so long as the generated error value is below this error tolerance value for the target output variable PPM of NOx. In another embodiment, all values of a target output variable are to be considered when the respective absolute error tolerance is assigned a value of zero.

In addition to an absolute error value, a relative error tolerance may be assigned to a target output variable. In an embodiment, a relative error tolerance value may be expressed as a percentage of a target output variable predicted by the master mechanism. For example, if "Crank Angle at 10% of heat-release" ("CA10") is selected as a target output variable, and solving the master mechanism predicts a CA10 value of approximately 7 degrees ATDC, setting a relative error tolerance of 20% for this target output variable would result in species being removed from the mechanism until the CA10 value is within 1.4 degrees of the value predicted by the master mechanism.

An embodiment may provide various options for expressing error values generated in the error calculations described below. These options may be provided in a list or menu, or selected from a library. For example, a generated error value may be expressed as the entire time/spatial profile of the respective target output variable over the entire species removal procedure. Alternately, the generated error value for a particular target output variable may be expressed as only the end-point value ("end point option") or the maximum error value generated in any iteration of the species removal procedure. In addition, for single-point target output variables such as ignition-delay time or flame speed, if the mechanism reduction process is performed iteratively, the "end point option" will employ only the error value generated from the final iteration, rather than employing values generated at each iteration of the process.

In embodiments of the present invention, operational parameters for the mechanism can be specified. More specifically, once error tolerances are assigned as seen at block 206 of FIG. 2, certain species may be designated as exempt from the species removal procedures, as shown at block 208. That is, in a mechanism reduction process 200, it may be desirable to specify that certain species are not replaced with isomers in an isomer reduction procedure. For example, in a mechanism associated with a combustion reaction model, key species such as the inlet species and other species that are major combustion products may be designated as exempt, so that they are not replaced by isomers in the reduced mechanism. The reduced mechanism would thus include these species and their properties rather than representative isomers and representative properties of isomer groups into which these species may otherwise have been categorized.

In another embodiment, if the target output variables selected at block 204 are to be evaluated over a wide range of reaction conditions, a subset of reaction conditions can be specified for the reduction process 200 (block 210), to simplify and make the mechanism reduction process 200 more manageable. Reducing complexity in this way reduces the run-time needed to generate the reduced mechanism, and may result in improved efficiency, particularly where the reaction conditions of interest are limited. Of course, the invention contemplates specification of other operational parameters for the mechanism reduction process (for example, reaction conditions or other reaction parameters, particularly when the mechanism reduction process is incorporated into a broader chemical reaction analysis).

In an embodiment of the invention, the master mechanism may include chemical reaction paths. In another embodiment, specifying the reaction conditions as discussed above (block 210) may also include defining a set of chemical reaction-flow models that represents certain operating conditions and in which the chemical reaction equations of the master mechanism may be conservation equations that include variables and mathematical terms derived from the chemical reaction model. Such chemical reaction equations and conservation equations may be expressed as mathematical equations that are operable and solvable. In such an embodiment, target output variables may be selected from the set of reaction-flow model conservation equations, and the conservation equations may be solved to generate master values for these variables. The chemical species in these reaction-flow model conservation equations may be categorized into isomer groups and replaced with representative isomers and properties and the conservation equations may be iteratively solved, with successive species replacement by isomers as discussed in greater detail below, to iteratively generate target output variables in the process of generating a reduced mechanism.

In order to control the mechanism reduction process through the use of error tolerances, in another embodiment, solutions are generated for the target output variables of interest, by solving the equations in the master mechanism for the selected target output variables. These solution values may be designated, recorded or stored as "master values" (block 212).

Once the target output variables are selected (block 204), error tolerances are assigned (block 206), any operational parameters are specified (blocks 208 and 210), and "master values" are generated (block 212), the isomer replacement procedure commences (block 214). This procedure, also known as isomer "lumping" includes aspects of the isomer "lumping" procedure described above, in connection with the "standalone" mechanism reduction process. That is, the lumping process categorizes, or "lumps," individual chemical species into isomer groups based on similarities in the species' molecular structures and properties. The categorization follows a set of one or more lumping rules, one or more of which may be predetermined, as set forth above in connection with the "standalone" mechanism reduction. In another embodiment, however, the lumping process may proceed in an iterative fashion, as shown at blocks 214, 216, 218, 220, 222 and 224. This means that each lumping rule in the set is applied in a cumulative, staged process, or in a discrete iteration, rather than at the same time that the other rules are applied, so that species are removed in a gradual fashion at each iteration, and the accuracy of the lumping process can be monitored and controlled. In other embodiments, the set of lumping rules to be applied may be wholly or partially selected from a list or library containing a set of lumping rules. In addition, the sequence of lumping rules may be predetermined, or may be determined during the iterative lumping rule application process, based on the interim results of the isomer lumping process.

For example, once the target output variables have been selected (block 204), error tolerances assigned (block 206), and any operational parameters specified (blocks 208, 210), all chemical species in the mechanism are analyzed and categorized based on based on similarities in the species' molecular structures and properties (as discussed above, the following functional groups are considered in the lumping process: hydroxy, hydroxyl radical, carbonyl, peroxide, peroxy radical, and carbon radical groups). Of course, the species designated as "exempt" from the lumping procedure at block 208 are not analyzed and categorized. In keeping with the iterative nature of the process of this embodiment, only a single (i.e., the "first") isomer lumping rule is applied at block 214 to categorize species. For example, the set of isomer lumping rules described above, in connection with the "standalone" lumping method may be applied, albeit in an iterative fashion. That is, rather than applying all of the isomer rules prior to generating a reduced mechanism, the first isomer lumping rule of the set is applied independently of the other rules, to generate a provisional mechanism in which species having the same number of each of the functional groups are lumped into the same isomer group.

Thus, the species belonging to isomer groups based on the first lumping rule are identified, and these species and their respective properties are replaced in the mechanism equations with representative isomers and representative isomer properties corresponding to the respective isomer group, as discussed above, to generate a provisional mechanism (block 216). Replacing each species in a particular isomer group with a single representative isomer in the mechanism means that all thermodynamic and transport properties of species belonging to an isomer group are replaced by properties of the respective representative isomer. Accordingly, all chemical reaction equations in the mechanism that involve a species in a particular isomer group are modified to include the respective representative isomer and the representative properties.

Because each representative isomer replaces a group of distinct chemical species, the thermodynamic and transport properties of a representative isomer may be combinations of the corresponding properties of each chemical species in the isomer group. Methods of accounting for the contributions of each chemical species are known in the art. For example, in the description of the standalone mechanism reduction process described above, an equi-repartition approach is applied, as described in S. S. Ahmed, G. Moreac, T. Zeuch, and F. Mauss, "Reduced Mechanism for the Oxidation of the Mixtures of n-Heptane and iso-Octane," European Combustion Meeting, 2005. This equi-repartition approach may be applied in an embodiment of an iterative isomer replacement procedure in accordance with the teachings of the invention.

However, the assumption that all isomers contribute exactly the same all the time can lead to lower accuracy of the lumped mechanism. Thus, another embodiment employs an alternative approach for accounting for the contribution of the chemical species grouped into an isomer group. This approach is the constant ratio approach described and used in T. Lu, and C. K. Law, "Strategies for Mechanism Reduction for Large Hydrocarbons: n-Heptane," *Combust. Flame,* 154: 153-163, 2008.

The constant ratio approach tracks the intra-group mass fraction of the species in each isomer group and uses the average mass fractions over all sampling points as the relative contribution of each species to the lumped species. It requires running simulations over the range of conditions of interest, using the master mechanism to calculate the average of the intra-group mass fractions.

II.A. Adjustment of Rate Constants

As discussed above in connection with the standalone mechanism reduction process, the rate constants of chemical reaction equations in which species have been replaced with representative isomers and representative properties may need adjustment to account for this change in properties. Adjustment of the rate constants may proceed as described in Section I.A., above. However, if the constant ratio approach is applied rather than the equi-repartition approach, the following adjustments to the chemical reaction equations must be made: in the constant ratio approach, $L_A$ equals the reciprocal of the average intragroup mass fraction of $A_i$ in the $\{A_i\}$ group and $L_B$ equals the reciprocal of the average intra-group mass fraction of $B_i$ in the $\{B_i\}$ group. Except for differences in the $L_A$ and $L_B$ values, the rate constants for the constant ratio approach are adjusted in the same manner as described in Section I.A., in connection with the equi-repartition approach. In an embodiment, the adjustment of rate constant occurs in conjunction at each iteration of the process that involves replacement of species with representative isomers (block 216).

Referring again to FIG. 2, the provisional mechanism is used to generate solutions for the selected target output variables, as shown at block 218. The solutions generated using the provisional mechanism are compared with the corresponding master values generated using the master mechanism, to generate a normalized error value for each target output variable (block 220). More specifically, the normalized error value for each target output variable is determined by the following equation:

$$\frac{|MV - PV|}{(R|MV| + A)}$$

wherein:
MV is the master value corresponding to the target output variable
PV is the value of the target output variable generated using the provisional mechanism
R is the relative error tolerance assigned to the target output variable
A is the absolute error tolerance assigned to the target output variable If the normalized error value for each target output variable is less than a predetermined threshold value, all assigned error tolerance settings are satisfied. In an embodiment, this predetermined threshold value may be 1.0. As shown at block 222, if all of the normalized error values for the target output variables are below the predetermined threshold, another isomer lumping rule in the set will be applied (block 224), and the isomer lumping procedure and rate constant adjustment steps will be repeated to generate a new provisional mechanism. At this point, more species will be replaced (block 216), solutions for target output variables will be generated (block 218), and a new set of normalized error values will be generated (block 220) for comparison with the predetermined threshold value (block 222). Since, as discussed above, removing more species from the mechanism increases the normalized error values, applying isomer lumping rules in an iterative process results in the replacement of more species with representative isomers and an increase the normalized error values at each successive step.

In one embodiment of the present invention the same series of isomer lumping rules as set forth in the above description regarding the "standalone" mechanism reduction process is applied, albeit in an iterative process. That is, each isomer lumping rule set forth above is applied sequentially, and a new provisional mechanism is generated each time a successive isomer lumping rule is applied. In alternative embodiments of the present invention, the lumping rules may be applied in a different order than they appear in the series described above, or other lumping rules may be applied without departing from the inventive concepts. In addition, each provisional mechanism and the associated normalized error values that are generated may be recorded or stored for later access or retrieval.

The process of sequentially applying isomer lumping rules, generating provisional mechanisms and normalized error values and comparing the normalized error values with a predetermined threshold value continues, as shown at blocks 216-224, until a normalized error value meets or exceeds the predetermined threshold value. At this point, the iterative process terminates and the provisional mechanism with the fewest number of species and in which no normalized error value exceeds the predetermined threshold is designated, output or stored as a reduced mechanism (block 226). The process may also be terminated if all isomer lumping rules in a set are applied and no normalized error value greater than the threshold value is generated. In this case, the provisional mechanism with the fewest isomers may be output, identified, designated, or stored as the reduced mechanism.

In embodiments of the invention, the iterative isomer reduction process may be monitored by tracking the normalized error values as they are generated and the process may be stopped at any point. The mechanism reduction process according to the invention may also provide for selection and retrieval or access of any provisional mechanisms generated during the isomer lumping procedure, for use in modeling chemical reactions. This allows for great flexibility in analyzing chemical reaction models.

III. Computing Apparatus and Systems

It is understood that the various embodiments of the present invention may be implemented individually, or collectively, in devices comprised of various hardware and/or software modules and components. Such a device, for example, may comprise a processor, a memory unit, and an interface that are communicatively connected to each other, and may range from desktop, server and/or laptop computers, to consumer electronic devices such as mobile devices and the like. Such devices may include input and peripheral devices, and other components that enable the device to read and receive data and instructions from various media, input devices, a network, or other inputting means in accordance with the various embodiments of the invention. It should be understood, however, that the scope of the present invention is not intended to be limited to one particular type of device.

As an example, FIG. 3 illustrates a block diagram of a device 300 within which the various embodiments of the present invention may be implemented. The device 300 comprises at least one processor 304 and/or controller, at least one memory unit 302 that is in communication with the processor, and at least one communication unit 306 that enables the exchange of data and information, directly or indirectly, with a communication medium, such as the Internet, or other networks, entities and devices. The processor 304 can execute program code that is, for example, stored in the memory 302. The communication unit 306 may provide wired and/or wireless communication capabilities in accordance with one or more communication protocols and interfaces, and therefore it may comprise the proper transmitter/receiver antennas, circuitry and ports, as well as the encoding/decoding capabilities that may be necessary for proper transmission and/or reception of data and other information. The device 300 may further include various other components, such as a display for providing output to the user and an input interface (e.g., keyboard, mouse, etc.).

Similarly, the various components or sub-components within each module of the present invention may be implemented in software, hardware, and/or firmware. The connectivity between the modules and/or components within the modules may be provided using any one of a variety of connectivity methods and media, including, but not limited to, communications over the Internet, wired, or wireless networks using the appropriate protocols.

IV. Chemical Reaction

The results from the model may be used to achieve desired results in a chemical reaction. For example, a chemical reaction using the chemical species lumped in the model mechanism may be caused to take place to achieve results that are substantially similar to those produced by the chemical reaction model using the lumping. In this regard, the tolerances used in the lumping can dictate the accuracy of the result.

Various embodiments described herein are described in the general context of method steps or processes, which may be implemented in one embodiment by a computer program product or module, embodied in a computer-readable memory, including computer-executable instructions, such as program code, and executed by apparatus such as computers or computing systems in networked environments. A computer-readable memory may include removable and non-removable storage devices including, but not limited to, Read Only Memory (ROM), Random Access Memory (RAM), compact discs (CDs), digital versatile discs (DVD), etc. As such, the various disclosed embodiments can be implemented by computer code embodied on non-transitory computer readable media. In other embodiments processes may be employed to perform operations on data, wherein the instructions for process operations and the data, or elements thereof, may reside on or be transferred through one or more computing devices or systems.

Embodiments of the present invention may be implemented in software, hardware, application logic or a combination of software, hardware and application logic. The software, application logic and/or hardware may reside on a client device, a server or a network component. If desired, part of the software, application logic and/or hardware may reside on a client device, part of the software, application logic and/or hardware may reside on a server, and part of the software, application logic and/or hardware may reside on a network component. In an example embodiment, the application logic, software or an instruction set is maintained on any one of various conventional computer-readable media. In the context of this document, a "computer-readable medium" may be any media or means that can contain, store, communicate, propagate or transport the instructions for use by or in connection with an instruction execution system, apparatus, or device, such as a computer, with one example of such a device described and depicted in FIG. 3. A computer-readable medium may comprise a computer-readable storage medium that may be any media or means that can contain or store the instructions for use by or in connection with an instruction execution system, apparatus, or device, such as a computer. In one embodiment, the computer-readable storage medium is a non-transitory storage medium.

In various respects, embodiments of the present invention my use data from a database. For example, a database of chemical species may be accessed to obtain various properties of the chemical species. Other data described in this disclosure may be similarly obtained from or stored in a database.

If desired, the different functions discussed herein may be performed in a different order and/or concurrently with each other. Furthermore, if desired, one or more of the above-described functions may be optional or may be combined.

Although various aspects of the invention are set out in the independent claims, other aspects of the invention comprise other combinations of features from the described embodiments and/or the dependent claims with the features of the independent claims, and not solely the combinations explicitly set out in the claims.

The foregoing description of embodiments has been presented for purposes of illustration and description. The foregoing description is not intended to be exhaustive or to limit embodiments of the present invention to the precise form disclosed, and modifications and variations are possible in light of the above teachings or may be acquired from the practice of various embodiments. The embodiments discussed herein were chosen and described in order to explain the principles and the nature of various embodiments and its practical application to enable one skilled in the art to utilize the present invention in various embodiments and with various modifications as are suited to the particular use contemplated. The features of the embodiments described herein may be combined in all possible combinations of methods, apparatus, modules, systems, and computer program products.

What is claimed is:

1. A processor implemented method for building or modifying a physical system by determining the results of a chemical reaction model by executing a reduced-complexity reaction model of the chemical reaction model, the method comprising:
   extracting physical data associated with the physical system including a master chemical mechanism associated with the physical system to generate a chemical reaction model for the physical system;
   obtaining data for one or more chemical species in the chemical reaction model from a database, the database including properties of the one or more chemical species, wherein the chemical reaction model includes data representing the reactions and chemical species based on mathematical equations in a chemical process;
   grouping the chemical species in the chemical reaction model into one or more isomer groups according to molecular properties of the chemical species;
   assigning a representative isomer to at least one isomer group;
   generating a second chemical reaction model based on replacement of a plurality of chemical species of a particular group with a corresponding representative isomer assigned to that particular group according to the chemical reaction model; and
   executing the second chemical reaction model by an apparatus to determine results without executing the chemical reaction model generated via said extracting, the results determined for building or modifying the physical system.

2. The method of claim 1, further comprising:
   causing a chemical reaction to take place using the one or more chemical species, the chemical reaction corresponding to the chemical reaction model.

3. The method of claim 1, wherein the operation of grouping the chemical species into one or more isomer groups further comprises:
   specifying an allowable difference of a thermodynamic property among the chemical species in a particular isomer group; and
   dividing an isomer group into sub-groups if the allowable difference is exceeded.

4. The method of claim 1, wherein the chemical species are grouped into one or more isomer groups based on one or more lumping rules.

5. The method of claim 4, wherein the chemical species are sorted based on molecular properties according to one of the one or more lumping rules.

6. The method of claim 4, wherein at least one of the one or more lumping rules is predetermined.

7. The method of claim 1, wherein representative isomer properties are calculated as a function of the relative contribution of each chemical species in an isomer group.

8. The method of claim 1, wherein at least one of the chemical reaction equations is based on one or more rate values and an equilibrium value, and the operation of replacing chemical species with representative isomers further includes adjusting at least one of the equilibrium value and one or more rate values.

9. The method of claim 1, wherein the second chemical reaction model includes fewer chemical species than the chemical reaction model.

10. An apparatus for building or modifying a physical system by determining the results of a chemical reaction model, the apparatus comprising:
    at least one processor; and
    at least one memory including computer program code, the at least one memory and the computer program code configured to, with the at least one processor, cause the apparatus to perform at least the following:
    extracting physical data associated with the physical system including a master chemical mechanism associated with the physical system to generate a chemical reaction model for the physical system;
    obtaining data for one or more chemical species in the chemical reaction model from a database, the database including properties of the one or more chemical species, wherein the chemical reaction model includes data representing the reactions and chemical species based on mathematical equations in a chemical process;
    grouping the chemical species in the chemical reaction model into one or more isomer groups according to molecular properties of the chemical species;
    assigning a representative isomer to at least one isomer group;
    generating a second chemical reaction model based on replacement of a plurality of chemical species of a particular group with a corresponding representative isomer assigned to that particular group according to the chemical reaction model; and
    executing the second chemical reaction model to determine results without executing the chemical reaction model generated via said extracting, the results determined for building or modifying the physical system.

11. The apparatus of claim 10, wherein the apparatus further performs the step of:
    causing a chemical reaction to take place using the one or more chemical species, the chemical reaction corresponding to the chemical reaction model.

12. The apparatus of claim 10, wherein an allowable threshold is specified for differences of a thermodynamic property among the chemical species in a particular isomer group, wherein the operation of grouping the chemical species into one or more isomer groups further comprises:
    dividing an isomer group into sub-groups if the maximum allowable difference is exceeded.

13. The apparatus of claim 10, wherein the chemical species are grouped into one or more isomer groups based on one or more lumping rules.

14. The apparatus of claim 13, wherein the chemical species are sorted based on molecular properties according to one of the one or more lumping rules.

15. The apparatus of claim 13, wherein at least one of the one or more lumping rules is predetermined.

16. The apparatus of claim 10, wherein representative isomer properties are calculated as a function of the relative contribution of each chemical species in an isomer group.

17. The apparatus of claim 10, wherein at least one of the chemical reaction equations is based on one or more rate values and an equilibrium value, and the operation of replacing chemical species with representative isomers further includes adjusting at least one of the equilibrium value and one or more rate values.

18. The apparatus of claim 10, wherein the second chemical reaction model includes fewer chemical species than the chemical reaction model.

19. An apparatus for building or modifying a physical system by determining the results of a chemical reaction model by executing a reduced-complexity reaction model of the chemical reaction model, the apparatus comprising:
  at least one processor; and
    at least one memory including computer program code, the at least one memory and the computer program code configured to, with the at least one processor, cause the apparatus to perform at least the following:
    extracting physical data associated with the physical system including a master chemical mechanism associated with the physical system to generate a chemical reaction model for the physical system;
    obtaining data for one or more chemical species in a chemical reaction model from a database, the database including properties of the one or more chemical species, wherein the chemical reaction model includes mathematical equations and data representing the reactions and chemical species in a chemical process;
    grouping the chemical species in a chemical reaction model into one or more isomer groups according to molecular properties of the chemical species;
    assigning a representative isomer to at least one isomer group;
    replacing, in one or more chemical reaction equations of the chemical reaction model, a plurality of chemical species of a particular group with a corresponding representative isomer assigned to that particular group to generate a second chemical reaction model; and
  executing the second chemical reaction model by an apparatus to determine results, wherein processing time is reduced by said executing the second chemical reaction model instead of executing the chemical reaction model generated via said extracting;
  wherein the physical system is built or modified based on the determined results.

* * * * *